United States Patent
Laurencin et al.

(10) Patent No.: US 12,091,522 B2
(45) Date of Patent: Sep. 17, 2024

(54) GRAPHENE COMPOSITE MATRICES AND USES THEREOF

(71) Applicant: University of Connecticut, Farmington, CT (US)

(72) Inventors: Cato Laurencin, Farmington, CT (US); Leila Daneshmandi, Farmington, CT (US)

(73) Assignee: UNIVERSITY OF CONNECTICUT, Farmington, CT (US)

( * ) Notice: Subject to any disclaimer, the term of this patent is extended or adjusted under 35 U.S.C. 154(b) by 353 days.

(21) Appl. No.: 17/598,428

(22) PCT Filed: Mar. 31, 2020

(86) PCT No.: PCT/US2020/025906
§ 371 (c)(1),
(2) Date: Sep. 27, 2021

(87) PCT Pub. No.: WO2020/205831
PCT Pub. Date: Oct. 8, 2020

(65) Prior Publication Data
US 2022/0177664 A1 Jun. 9, 2022

Related U.S. Application Data

(60) Provisional application No. 62/828,149, filed on Apr. 2, 2019.

(51) Int. Cl.
C08J 9/24 (2006.01)
C08J 9/00 (2006.01)
C08K 3/04 (2006.01)

(52) U.S. Cl.
CPC ............... *C08J 9/0066* (2013.01); *C08J 9/24* (2013.01); *C08K 3/042* (2017.05); *C08J 2205/044* (2013.01); *C08J 2207/10* (2013.01); *C08J 2367/04* (2013.01)

(58) Field of Classification Search
CPC ...... C08J 9/0066; C08J 9/24; C08J 2205/044; C08J 2207/10; C08J 2367/04; C08K 3/042; A61L 2430/02; A61L 2430/12; A61L 27/38; A61L 2300/414; A61L 27/443; A61L 27/54; A61L 27/56; C01B 32/198

See application file for complete search history.

(56) References Cited

FOREIGN PATENT DOCUMENTS

CN 105297168 A * 2/2016

OTHER PUBLICATIONS

Araújo et al., "Tuning the surface chemistry of graphene flakes: new strategies for selective oxidation," RSC Advances, 2017, 7, 14290-14301. (Year: 2017).*
International Search Report and Written Opinion mailed Jun. 18, 2020 in International Application No. PCT/US2020/025906, filed Mar. 31, 2020, 12 pages.

(Continued)

*Primary Examiner* — K. Boyle
(74) *Attorney, Agent, or Firm* — McDonnell Boehnen Hulbert & Berghoff LLP

(57) ABSTRACT

The disclosure provides porous scaffold that include a plurality of microspheres, where the microspheres include a biodegradable polymer blended with a graphene family material (GFM), micro spheres, and methods for making and using such scaffolds and microspheres.

18 Claims, 6 Drawing Sheets

(56) References Cited

OTHER PUBLICATIONS

Figure 1:
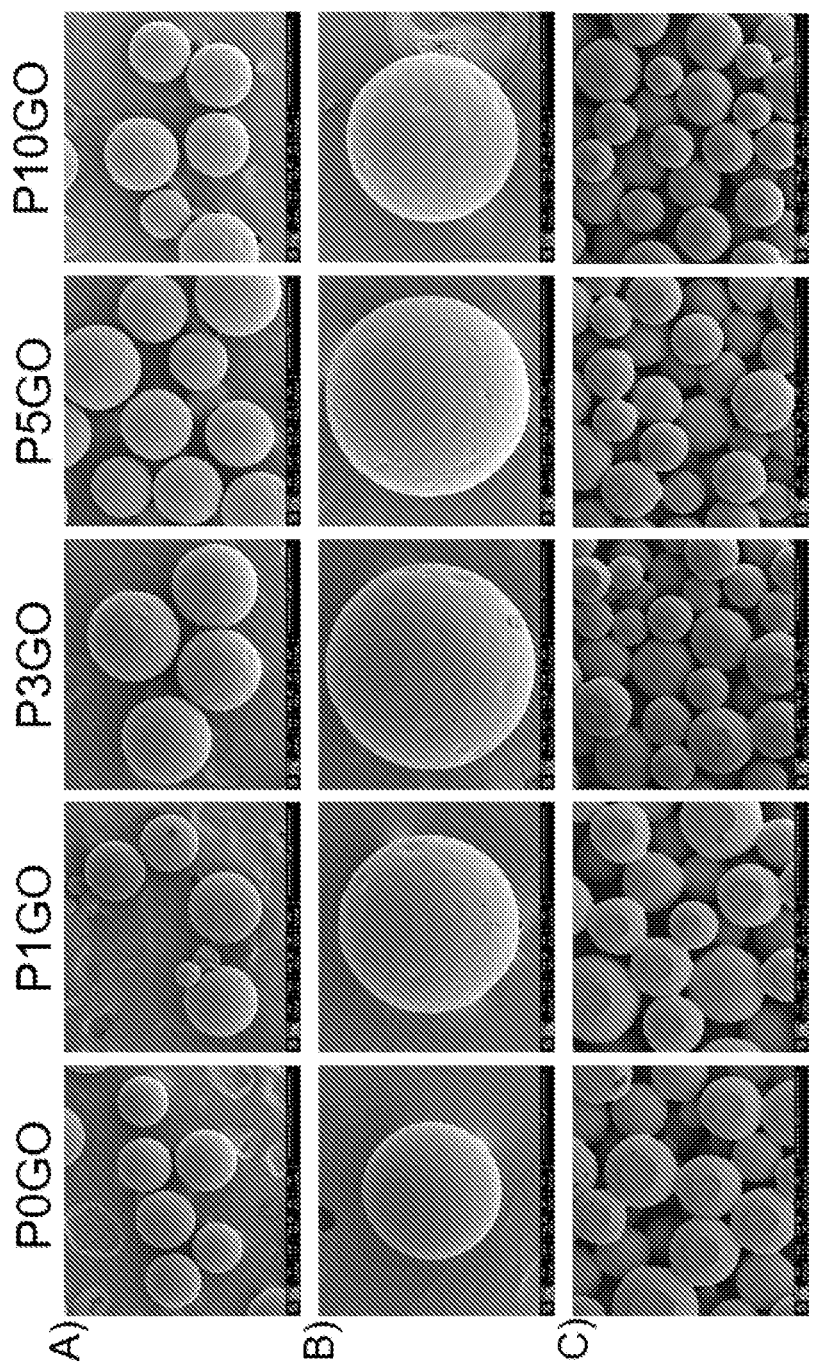

Fu et al., "Enhancing Cell Proliferation and Osteogenic Differentiation of MC3T3-E1 Pre-osteoblasts by BMP-2 Delivery in Graphene Oxide-Incorporated PLGAIHA Biodegradable Microcarriers," Scientific Reports, vol. 7, Oct. 2, 2017, pp. 1-13.

Zhang et al., "Mass-production of nuorescent chitosan/graphene oxide hybrid microspheres for in vitro 3D expansion of human umbilical cord mesenchymal stem cells," Chemical Engineering Journal, vol. 331, Sep. 7, 2017, pp. 675-684.

Holt, B. D., et al. Graphene oxide as a scaffold for bone regeneration. Wiley Interdiscip Rev Nanomed Nanobiotechnol. May 2017;9(3). doi: 10.1002/wnan.1437. Epub Oct. 26, 2016. PMID: 27781398.

Mauffrey C, et al. Bone graft harvest site options in orthopaedic trauma: a prospective in vivo quantification study. Injury. Mar. 2012; 43(3):323-6. doi: 10.1016/j.injury.2011.08.029. Epub Sep. 13, 2011. PMID: 21917258.

\* cited by examiner

GRAPHENE COMPOSITE MATRICES AND USES THEREOF

CROSS REFERENCE

This application claims priority to U.S. Provisional Patent Application Ser. No. 62/828,149 filed Apr. 2, 2019, incorporated by reference herein in its entirety.

STATEMENT OF GOVERNMENT RIGHTS

This application is a U.S. national phase of International Application No. PCT/US2020/025906, filed on Mar. 31, 2020, which claims priority to U.S. Provisional Patent Application Ser. No. 62/828,149 filed Apr. 2, 2019, both of which are incorporated by reference herein in its their entirety.

BACKGROUND

Each year, approximately 2.2 million bone graft procedures are performed worldwide. Current clinical treatments have only shown success for smaller sized bone defects and have significant limitations. Designing biodegradable matrices that are mechanically competent and biologically active has been a challenge. The current gold standard for bone regenerative engineering is using autografts (bone grafts taken from a donor site to a recipient site during surgery), which has significant drawbacks including limited supply, prolonged operation times, risk of donor site infection and morbidity. Allografts (bone grafts from human donors) are an alternative however they are associated with complications such as disease transmission, infection and immunogenicity. Synthetic bone graft prepared to date primarily fail to enhance bone healing and regenerate the tissue.

SUMMARY

In one aspect, the disclosure provides porous scaffolds, comprising a plurality of microspheres, wherein the microspheres comprise a biodegradable polymer blended with a graphene family material (GFM), selected from the group consisting of graphene oxide, reduced graphene oxide, functionalized derivatives thereof, or combinations thereof. In another embodiment, the GFM may be present in single layers or in multi-layers. In one embodiment, the plurality of microspheres are joined to form a scaffold, including but not limited to sintered together. In another embodiment, the polymer comprises poly(L-lactic-co-glycolic acid) (PLGA). In one embodiment, the GFM is encapsulated in the polymer microspheres. In various embodiments, the GFM is present at between about 1% to about 10%, about 1% to about 5%, or about 3% to about 5% as a wt % of the scaffold. In another embodiment, the microspheres are between about 100 μm in diameter and about 1000 μm in diameter, or between about 300 μm and 600 μm in diameter. In one embodiment, a ratio of carbon atoms to oxygen atoms of the GFM is between about 2:1 to about 4:1. In a further embodiment, at least 50% of the microspheres are joined to one or more other microspheres in the scaffold. In another embodiment, the scaffold is between about 1 mm×1 mm and about 20 mm×20 mm (diameter×height). In one embodiment, the scaffolds further comprise cells, growth factors, small molecules, therapeutics, and/or diagnostic agents associated with the scaffold.

In another aspect, the disclosure provides methods for use of the scaffolds of any embodiment or combination of embodiment of the disclosure for replacement and/or regeneration of bone tissue. In various embodiment embodiments, the replacement and/or regeneration of bone tissue may comprise bone grafting procedures including but not limited to the treatment of segmental bone loss caused by trauma, tumor excision, infection, non-unions, osteonecrosis or developmental deformities for long bone, spinal fusion, craniomaxillofacial, foot and ankle, dental and joint reconstruction.

In a further aspect, the disclosure provides methods for making the porous scaffold of any embodiment or combination of embodiment of the disclosure, as described herein.

FIGURE LEGENDS

FIG. 1A-C. Scanning electron micrographs of (A, B) PLGA and the composite PLGA/GO microspheres and (C) the sintered microsphere scaffolds (original magnification 100× and 250×.)

Figure 2:
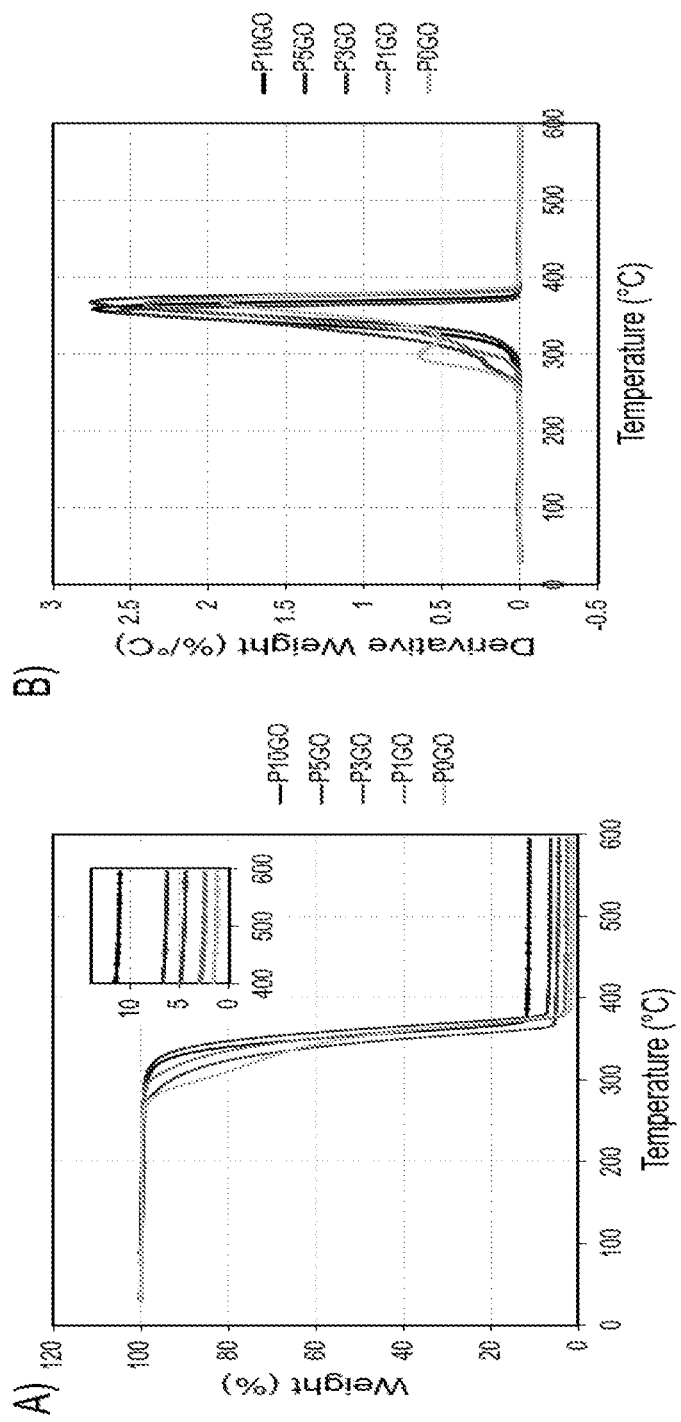
Figure 3:
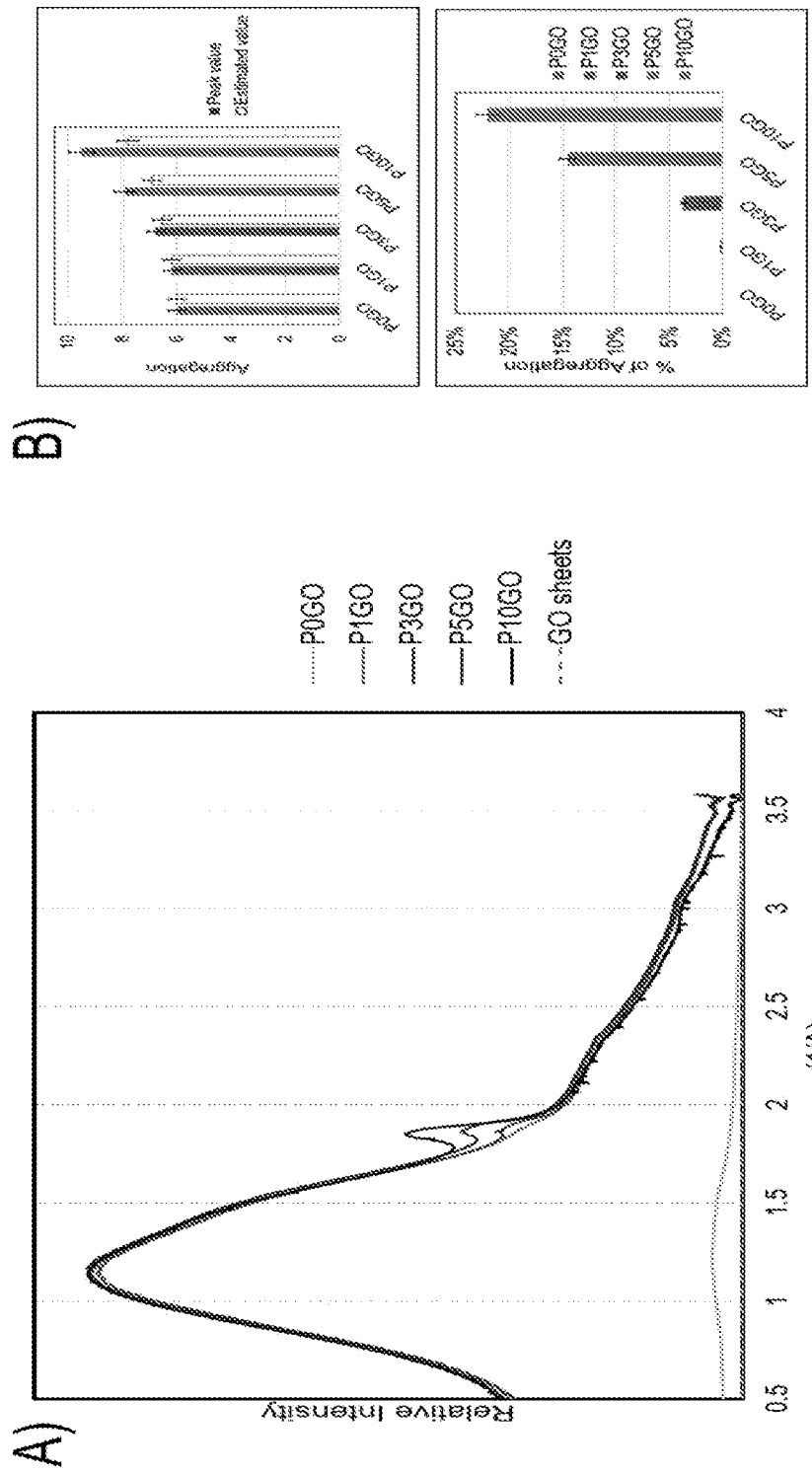
Figure 4:
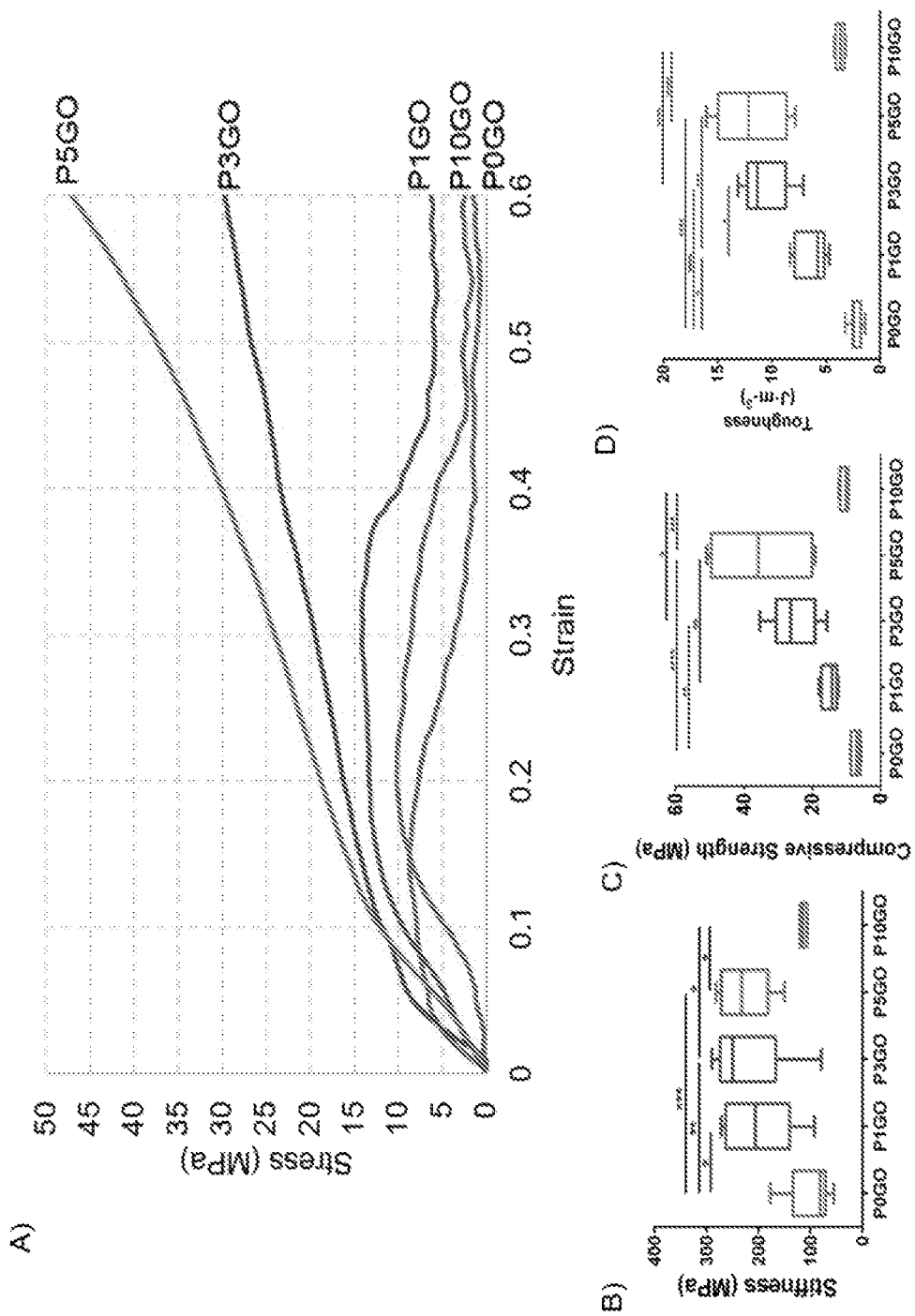

FIG. 2A-B. (A) TGA thermograms of composite microspheres. (B) TGA first derivative curves of composite microspheres FIG. 3A-B. (A) Wide angle x-ray scattering of the PLGA and PLGA/GO composite microsphere scaffolds. (B) Aggregation of the GO sheets within the PLGA microspheres FIG. 4A-D. Mechanical properties of the PLGA and PLGA/GO microsphere scaffolds. (A) Representative stress-strain curves for all microsphere scaffolds under uniaxial compressive loading. (B) Stiffness, (C) compressive strength, and (D) toughness values of the PLGA and various compositions of PLGA/GO composite microsphere scaffolds.

Figure 5:
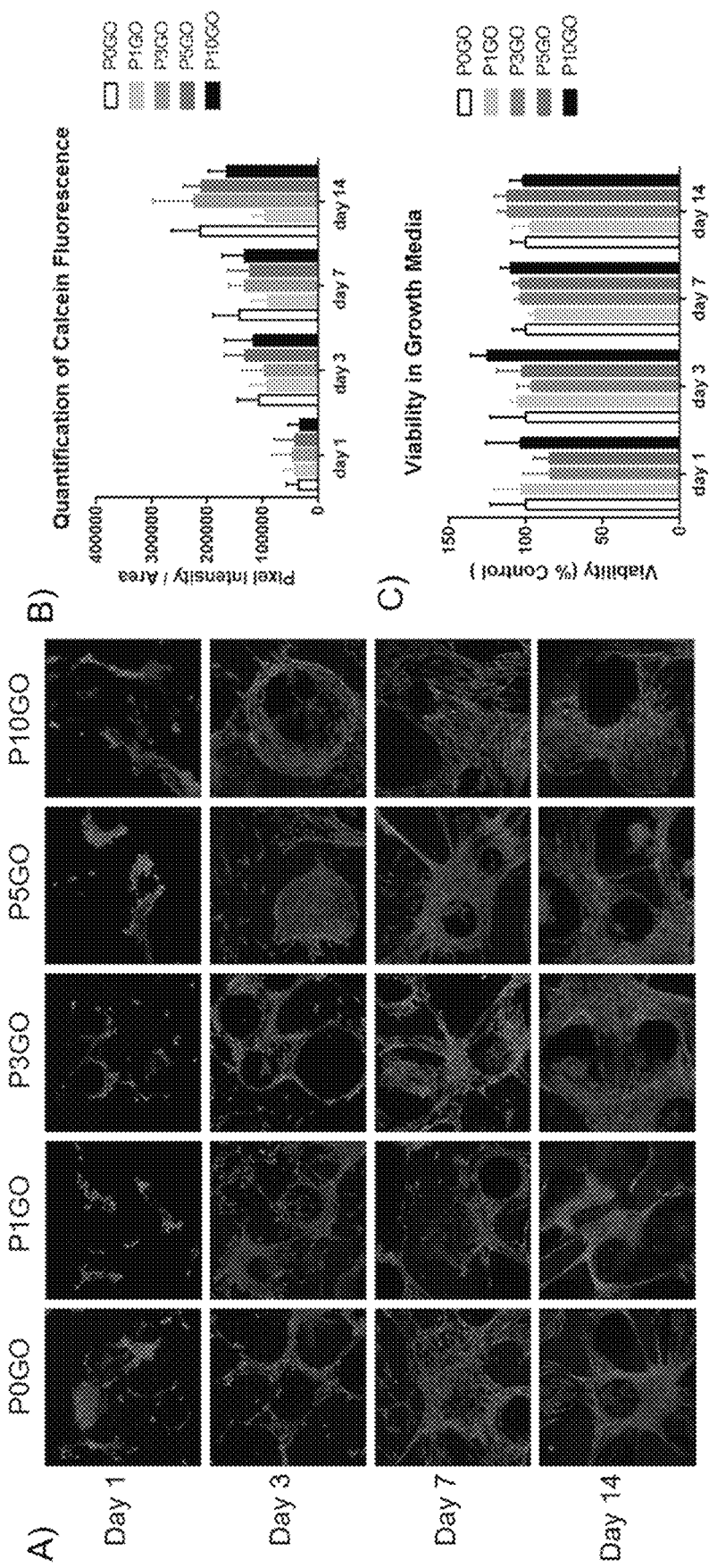

FIG. 5A-C. Cytocompatibility of the microsphere scaffolds. (A) Top-down view, laser-scanning confocal image reconstructions of hADSCs cultured on PLGA and the PLGA/GO composite scaffolds. Cells have been labelled with calcein AM (green) for live cells and ethidium homodimer-1 (red) for dead cells. (B) Quantification of the intensity levels of calcein fluorescence. (C) Viability of hADSCs cultured on PLGA and the PLGA/GO composite scaffolds, as measured using the CCK-8 kit.

Figure 6:
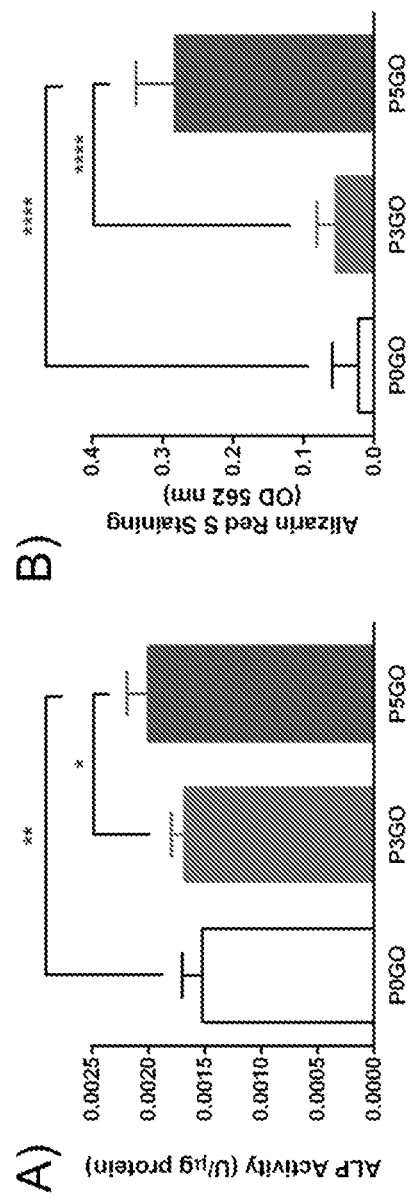

FIG. 6A-B. Osteogenic differentiation of hADSCs on the PLGA and PLGA/GO composite scaffolds. (A) ALP activity and (B) Alizarin Red S staining and quantification of the calcium mineral depositions at day 28.

DETAILED DESCRIPTION

All references cited are herein incorporated by reference in their entirety. Within this application, unless otherwise stated, the techniques utilized may be found in any of several well-known references such as: *Molecular Cloning: A Laboratory Manual* (Sambrook, et al., 1989, Cold Spring Harbor Laboratory Press), *Gene Expression Technology* (Methods in Enzymology, Vol. 185, edited by D. Goeddel, 1991. Academic Press, San Diego, CA), "Guide to Protein Purification" in *Methods in Enzymology* (M. P. Deutshcer, ed., (1990) Academic Press, Inc.); *PCR Protocols: A Guide to Methods and Applications* (Innis, et al. 1990. Academic Press, San Diego, CA), *Culture of Animal Cells: A Manual of Basic Technique*, 2$^{nd}$ Ed. (R.I. Freshney. 1987. Liss, Inc. New York, NY), *Gene Transfer and Expression Protocols*, pp. 109-128, ed. E. J. Murray, The Humana Press Inc., Clifton, N.J.), and the Ambion 1998 Catalog (Ambion, Austin, TX).

As used herein, the singular forms "a", "an" and "the" include plural referents unless the context clearly dictates otherwise.

As used herein, the term about means±5% of the recited parameter.

All embodiments of any aspect of the disclosure can be used in combination, unless the context clearly dictates otherwise.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to". The words "herein," "above," and "below" and words of similar import, when used in this application, shall refer to this application as a whole and not to any particular portions of the application.

The description of embodiments of the disclosure is not intended to be exhaustive or to limit the disclosure to the precise form disclosed. While the specific embodiments of, and examples for, the disclosure are described herein for illustrative purposes, various equivalent modifications are possible within the scope of the disclosure, as those skilled in the relevant art will recognize.

In one aspect, the disclosure provides porous scaffolds, comprising a plurality of microspheres, wherein the microspheres comprise a biodegradable polymer blended with a GFM selected from the group consisting of graphene oxide, reduced graphene oxide, functionalized derivatives thereof, or combinations thereof.

The present disclosure provides a composite system that is fabricated of microspheres (exemplified by PLGA) and a GFM, exemplified by graphene oxide. The scaffold may be biocompatible and biodegradable, behaves similar to trabecular bone and can serve as an effective scaffold for the replacement and regeneration of bone tissue. The scaffolds are demonstrated to have surprisingly robust mechanical properties, and are particularly useful, in non-limiting examples, by orthopedic surgeons for use in bone grafting procedures including but not limited to the treatment of segmental bone loss caused by trauma, tumor excision, infection, non-unions, osteonecrosis or developmental deformities for long bone, spinal fusion, craniomaxillofacial, foot and ankle, dental and joint reconstruction.

The scaffolds disclosed herein avoid the necessity of a second surgery to obtain autografts. This would reduce infection, tissue morbidity, pain, prolonged surgery time, complications with anesthesia, bleeding, blood clots, and nerve damage. Additionally it would save the surgeon's time thus saving money for the hospital.

As used herein, a "microsphere" is a spherical particle comprising a biodegradable polymer, with the microsphere having a diameter in the micrometer or nanometer range. In one embodiment, the microspheres have diameters in the micrometer range (i.e. 1 µm to 1000 µm). The diameters may be any that are suitable for an intended use of the scaffold. In one embodiment, the microspheres are 50 µm or greater in diameter (i.e., 50 µm, 100 µm, 150 µm, 200 µm, 250 µm, 300 µm, 350 µm, 400 µm, 450 µm, 500 µm, or greater in diameter. In another embodiment, the microspheres are between about 100 µm in diameter and about 1000 µm in diameter, or between about 300 µm and 600 µm in diameter.

The microspheres may comprise, consist essentially of, or consist of any polymer or combination of polymers suitable for an intended use. The polymers may be biodegradable. Exemplary such polymers include, but are not limited to, polylactides, polyglycolides, polycaprolactones, polyanhydrides, polyamides, polyurethanes, polyesteramides, polyorthoesters, polydioxanones, polyacetals, polyketals, polycarbonates, polyorthocarbonates, polyphosphazenes, polyhydroxybutyrates, polyhydroxyvalerates, polyalkylene oxalates, polyalkylene succinates, poly(malic acid), poly(amino acids), polyvinylpyrrolidone, polyethylene glycol, polyhydroxycellulose, chitin, chitosan, poly(L-lactic acid), poly(lactide-co-glycolide), poly(hydroxybutyrate-co-valerate), and copolymers, terpolymers, or combinations or mixtures of the above materials. In one specific embodiment, the polymer comprises, consists essentially of, or consists of poly (lactide-co-glycolide acid) (PLGA).

The scaffolds comprise a plurality of microspheres. The plurality of microspheres may comprise microspheres of the same/similar diameter, or may comprise microspheres of a variety of diameters. The number of microspheres suitable for a given scaffold can be determined by those of skill in the art based on the teachings herein in light of the size of the scaffold and its intended use.

The microspheres in scaffold are "joined," in that at least some adjoining microspheres share surface area. In some embodiments, a majority of microspheres (more than 50%, 55%, 60%, 65%, 70%, 75%, 80%, 85%, 90%, 95%, 96%, 97%, 98%, 99%, or 100%) in the scaffold are joined to one or more other microspheres. The microspheres can be joined via any suitable method, including but not limited to sintering, such as thermal or chemical sintering. Sintering can be carried out for any time and under any conditions suitable to join the microspheres, and will depend at least in part on the composition of the microspheres. Determining appropriate sintering conditions will be well within the level of those of skill in the art based on the teachings herein. In one embodiment, liquid sintering is used, wherein the liquid comprises a solvent/non-solvent composition appropriate for the polymer used. A "solvent/non-solvent composition" is a solvent system having at least two fractions: a volatile organic fraction (the solvent) and a non-volatile, typically aqueous, fraction. Any solvent/non-solvent composition suitable for the microspheres can be used. In one embodiment, the solvent/non-solvent composition has an organic solvent fraction and an aqueous (non-solvent) fraction. Appropriate solvent fractions include, but are not limited to, acetonitrile, acetone, hexanes, dichloromethylene, methanol, ethanol, and methylethylketone. Solvent/non-solvent compositions include acetone:water (e.g. 3:1) and acetonitrile:water (e.g. 8:1).

The resulting scaffold may be of any suitable size or shape for an intended purpose. As will be understood by those of skill in the art, any size or shape scaffold can be made by using an appropriate mold. In one non-limiting embodiment, the scaffold comprises a disc or cylindrical shape. In a further non-limiting embodiment, the scaffolds may be between about 1 mm×1 mm and about 20 mm×20 mm (diameter×height). The scaffold can also be engineered after the anatomical shape of a defect it is designed for.

The scaffold is porous, and the level of porosity can be adjusted through use of a porogen during scaffold production, as deemed appropriate in light of an intended use for the scaffold. In one non-limiting embodiment, the pore volume (%) is between about 20% to about 45%. In another non-limiting embodiment, the pore diameter may range between about 50 µm and about 450 µm, or between about 150 µm and about 200 µm.

The microspheres comprise a polymer, including but not limited to a biodegradable polymer, blended with a GFM. Graphene is an allotrope of carbon in the form of a single layer of carbon atoms in a two-dimensional hexagonal lattice. Graphene oxide (GO) is the oxidized form of graphene which is produced by oxidation and exfoliation of graphite. Reduced graphene oxide (RGO) is the form of GO that is processed by chemical, thermal and other methods in order to reduce the oxygen content. In various embodiments, the GFM comprises graphene oxide, reduced graphene oxide, or functionalized derivatives thereof. Functionalized GO or RGO are GO or RGO that include additional functional moieties, including but not limited to hydroxyl, epoxy, carboxyl, calcium ions, phosphate ions, etc. They also provide handles for chemical modification or functionalization that can be employed for various purposes such as gene therapy, drug delivery and biosensors.

Any suitable molar ratio of carbon atoms to oxygen atoms of the GO sheet may be used. In one embodiment, the ratio of carbon atoms to oxygen atoms of the GO sheet may be in a range from about 2:1 to about 4:1, or about 2:1 to about 3:1.

As used herein, "blended" means that the GFM is mixed with the polymer to create a composite of the two. In one specific embodiment, the GFM is encapsulated in the polymer microspheres.

The GFM may be present in any suitable weight percentage of the scaffold. In one embodiment, the GFM is present at between about 1% to about 10% as a wt % of the scaffold. In another embodiment, the GFM is present at between about 1% to about 5% as a wt % of the scaffold. In a further embodiment, the GFM is present at between about 3% to about 5% as a wt % of the scaffold. As will be understood by those of skill in the art, the scaffold comprises a plurality of microspheres. In one embodiment, all of the microspheres in the scaffold comprise the GFM. In other embodiments, a portion (i.e.: at least 20%, 30%, 40%, 50%, 60%, 70%, 80%, 90%, 95%, 96%, 97%, 98%, 99%) of the microspheres in the scaffold comprise the GFM. As will be understood by those of skill in the art, the plurality of microspheres in the scaffold that comprise the GFM may comprise different amounts of the GFM. In one non-limiting embodiment, the scaffold may comprise 50% microspheres with no GFM, 25% comprising 5% of the GFM wt %, and 25% comprising 1% of the GFM wt %, such that the GFM is present at 3% as a wt % of the scaffold.

The scaffolds of all embodiments and combinations of embodiments disclosed herein may comprise further components as deemed appropriate for an intended use. In one embodiment, the scaffolds further comprise cells, growth factors, small molecules, therapeutics, and/or diagnostic agents associated with the scaffold. This embodiment further enhances the use of the scaffolds for use in promoting bone repair and regeneration. The cells and growth factors may promote proliferation and/or differentiation of cells of interest. Growth factors may be attached to the microspheres. Any suitable method for linking growth factors to the scaffold may be used. Any suitable cells and growth factors can be used as appropriate for an intended use of the scaffolds. In one embodiment, the cells may comprise stem cells, induced pluripotent stem cells, osteoblasts, chondrocytes, precursors thereof, and combinations thereof. In another embodiment, the growth factors may comprise bone morphogenetic protein (BMP) (including but not limited to BMP-1; BMP-2; BMP-3; BMP-4; BMP-5; BMP-6; BMP-7; BMP-8; BMP-9; BMP-10; BMP-11; BMP-12 BMP-13; BMP-15; BMP-16; BMP-17; and BMP-18), Cbfa 1, insulin-like growth factors, interleukin-1, interleukin-6, tumor necrosis factor, Wnt5a, fibroblast growth factor (FGF) (such as FGF2), transforming growth factors (TGFs) (including TGF-β1, TGF-β2, and TGF-β3), Vascular endothelial growth factors (VEGF) (such as VEGF-A, VEGF-B, VEGF-C, VEGF-D and VEGF-E), Connective tissue growth factors (CTGF) (such as CTGF-1, CTGF-2, and CTGF-4), Growth differentiation factors (GDFs) (such as GDF-1, GDF-2, GDF-3, GDF-7, GDF-10, GDF-11, and GDF-15), cartilage-derived morphogenic proteins (CDMPs) (such as CDMP-1 and CDMP-2), LIM mineralization proteins (LMPs) (such as LMP-1, LMP-2, and LMP-3) and combinations thereof.

In another embodiment, the scaffolds may further comprise antibiotics or immunosuppressive agents. Examples of antibiotics useful with the scaffolds include, but are not limited to, amoxicillin, beta-lactamases, aminoglycosides, beta-lactam (glycopeptide), clindamycin, chloramphenicol, cephalosporins, ciprofloxacin, erythromycin, fluoroquinolones, macrolides, metronidazole, penicillins, quinolones, rapamycin, rifampin, streptomycin, sulfonamide, tetracyclines, trimethoprim, trimethoprim-sulfamethoxazole, and vancomycin. Suitable immunosuppressive agents that can be included in the scaffolds, include but are not limited to, steroids, cyclosporine, cyclosporine analogs, cyclophosphamide, methylprednisone, prednisone, azathioprine, FK-506, 15-deoxyspergualin, and other immunosuppressive agents that act by suppressing the function of responding T cells. Other immunosuppressive agents include, but are not limited to, prednisolone, methotrexate, thalidomide, methoxsalen, rapamycin, leflunomide, mizoribine, brequinar, deoxyspergualin, and azaspirane (SKF 105685), Orthoclone (muromonab-CD3) cyclosporine, tacrolimus, mycophenolate motefil, of which the active metabolite is mycophenolic acid), azathioprine, glucocorticosteroids, adrenocortical steroids such as prednisone and prednisolone, methotrexate, methoxsalen, and sirolimus.

In another embodiment, the scaffolds may further comprise peptides, small drug molecules, and genetic material (such as DNA, RNA, microRNA, PNA).

In another aspect, the disclosure provides methods for replacement and/or regeneration of bone tissue, comprising transplanting a scaffold of any embodiment or combination of embodiments of the disclosure into a subject in need thereof, so as to effect replacement and/or regeneration of bone tissue in the subject. The subject may be any mammal, such as a human subject. In non-limiting embodiments, the subject may be in need of replacement and/or regeneration of bone tissue due to segmental bone loss caused by trauma, tumor excision, infection, non-unions, osteonecrosis or developmental deformities for long bone, spinal fusion, craniomaxillofacial, foot and ankle, and dental and joint reconstruction.

The methods may comprise use of a scaffold further comprising cells and/or growth factors associated with the scaffold. Any suitable cells and growth factors can be used as appropriate for an intended use of the scaffolds. In one embodiment, the cells may comprise stem cells, osteoblasts, chondrocytes, precursors thereof, and combinations thereof. In another embodiment, the growth factors may comprise bone morphogenetic protein (BMP) (including but not limited to BMP-1; BMP-2; BMP-3; BMP-4; BMP-5; BMP-6; BMP-7; BMP-8; BMP-9; BMP-10; BMP-11; BMP-12; BMP-13; BMP-15; BMP-16; BMP-17; and BMP-18), Cbfa 1, insulin-like growth factors, interleukin-1, interleukin-6, tumor necrosis factor, Wnt5a, fibroblast growth factor (FGF) (such as FGF2), transforming growth factors (TGFs) (including TGF-β1, TGF-β2, and TGF-β3), Vascular endothelial growth factors (VEGF) (such as VEGF-A, VEGF-B, VEGF-C, VEGF-D and VEGF-E), Connective tissue growth factors (CTGF) (such as CTGF-1, CTGF-2, and CTGF-4), Growth differentiation factors (GDFs) (such as GDF-1, GDF-2, GDF-3, GDF-7, GDF-10, GDF-11, and GDF-15), cartilage-derived morphogenic proteins (CDMPs) (such as CDMP-1 and CDMP-2), LIM mineralization proteins (LMPs) (such as LMP-1, LMP-2, and LMP-3) and combinations thereof.

The scaffolds for use in the methods disclosed herein may comprise any other suitable materials as deemed appropriate for a given purpose, including but not limited to antibiotics and immunosuppressive agents, including but not limited to those disclosed herein.

In another aspect, the disclosure provides microspheres, comprising a polymer blended with a GFM selected from the group consisting of graphene oxide, reduced graphene oxide, functionalized derivatives thereof, or combinations thereof. The mechanical properties of the microspheres can be used to reinforce, structures. For instance, the microspheres could be added to hydrogels or polymers during the fabrication process to reinforce them and make them more mechanically competent. The addition of the microspheres to these structures can also improve the biological performance of the constructs. The surface properties will allow for the adsorption of protein and growth factors that will stimulate biological activity. The microspheres can also improve the migration and growth of stem cells on the structures and enhance the differentiation of stem cells into bone cells. Moreover, the physicochemical and surface properties of the microspheres can enable the delivery of growth factors and therapeutic agents to organs or tissues for specific biological purposes. All embodiments and combination of embodiments of the microspheres for use in scaffolds are equally applicable in this aspect. In one embodiment, the microspheres have diameters in the micrometer range (i.e. 1 µm to 1000 µm). The diameters may be any that are suitable for an intended use of the scaffold. In one embodiment, the microspheres are 50 µm or greater in diameter (i.e., 50 µm, 100 µm, 150 µm, 200 µm, 250 µm, 300 µm, 350 µm, 400 µm, 450 µm, 500 µm, or greater in diameter. In another embodiment, the microspheres are between about 100 µm in diameter and about 1000 µm in diameter, or between about 300 µm and 600 µm in diameter. The microspheres may comprise, consist essentially of, or consist of any polymer or combination of polymers suitable for an intended use. The polymers may be biodegradable. Exemplary such polymers include, but are not limited to, polylactides, polyglycolides, polycaprolactones, polyanhydrides, polyamides, polyurethanes, polyesteramides, polyorthoesters, polydioxanones, polyacetals, polyketals, polycarbonates, polyorthocarbonates, polyphosphazenes, polyhydroxybutyrates, polyhydroxyvalerates, polyalkylene oxalates, polyalkylene succinates, poly(malic acid), poly(amino acids), polyvinylpyrrolidone, polyethylene glycol, polyhydroxycellulose, chitin, chitosan, poly(L-lactic acid), poly(lactide-co-glycolide), poly(hydroxybutyrate-co-valerate), and copolymers, terpolymers, or combinations or mixtures of the above materials. In one specific embodiment, the polymer comprises, consists essentially of, or consists of poly (lactide-co-glycolide acid) (PLGA).

The microspheres comprise a polymer, including but not limited to a biodegradable polymer, blended with a GFM selected from the group consisting of graphene oxide, reduced graphene oxide, functionalized derivatives thereof, or combinations thereof. Functionalized GO or RGO are GO or RGO that include additional functional moieties, including but not limited to hydroxyl, epoxy, carboxyl, calcium ions, phosphate ions, etc. They also provide handles for chemical modification or functionalization that can be employed for various purposes such as gene therapy, drug delivery and biosensors.

Any suitable molar ratio of carbon atoms to oxygen atoms of the GO sheet may be used. In one embodiment, the ratio of carbon atoms to oxygen atoms of the GO sheet may be in a range from about 2:1 to about 4:1, or about 2:1 to about 3:1.

As used herein, "blended" means that the GFM is mixed with the polymer to create a composite of the two. In one specific embodiment, the GFM is encapsulated in the polymer microsphere. The GFM may be present in any suitable weight percentage of the microsphere. In one embodiment, the GFM is present at between about 1% to about 10% as a wt % of the microsphere. In another embodiment, the GFM is present at between about 1% to about 5% as a wt % of the microsphere. In a further embodiment, the GFM is present at between about 3% to about 5% as a wt % of the microsphere.

The microsphere of all embodiments and combinations of embodiments disclosed herein may comprise further components as deemed appropriate for an intended use. In one embodiment, the scaffolds further comprise cells, growth factors, small molecules, therapeutics, and/or diagnostic agents associated with the scaffold. This embodiment further enhances the use of the microsphere for use in promoting bone repair and regeneration. The cells and growth factors may promote proliferation and/or differentiation of cells of interest. Growth factors may be attached to the microspheres. Any suitable method for linking growth factors to the scaffold may be used.

In a further aspect, the disclosure provides methods for making the porous scaffold and microspheres of any embodiment or combination of embodiments, as described herein. In one embodiment, the method comprises:

(a) dissolving the polymer (including but not limited to PLGA) in a solvent (including but not limited to methylene chloride);
(b) mixing the dissolved polymer with a GFM (including but not limited to GO or rGO);
(c) dispersing the mixture in the solvent to generate a homogeneous suspension; and
(d) adding the suspensions into a solvent (including but not limited to polyvinyl alcohol) solution and stirring.

In a specific embodiment, PLGA and PLGA/GO microspheres were prepared using an oil-in-water emulsion solvent evaporation method. For pure PLGA microspheres, PLGA was dissolved in methylene chloride at a ratio of 1:7.5 (w/v). To prepare composite PLGA/GO microspheres, GO was mixed with PLGA at various concentrations of 1, 3, 5 and 10 wt. %. The mixture was then dispersed in methylene chloride and vortexed until a homogeneous suspension was obtained. The suspensions were then added via a thin stream into a 1% (w/v) PVA solution under a stirring speed of 250 rpm and left overnight. The resultant microspheres were then collected, rinsed with deionized water, dried by vacuum filtration, and lyophilized. The microspheres were subsequently sieved to 300-600 µm size ranges and packed into stainless steel molds and heated at 90° C. for 90 min to create 3D porous structures of 5 mm diameter×5 mm height, 5 mm diameter×15 mm height, 3.5 mm diameter×1 mm height, or anatomically engineered shapes and dimensions.

EXAMPLES

Summary

To engineer bone tissue, it is necessary to provide accurate spatiotemporal biochemical and mechanical stimuli to promote bone formation. Designing biodegradable scaffolds that are mechanically competent and biologically active has been a challenge. In this study, we fabricated composite microsphere scaffolds by incorporating GO sheets into poly (lactic-co-glycolic) acid (PLGA) microspheres. Results showed that the addition of GO reinforced the scaffolds by significantly improving the mechanical strength, stiffness, and toughness values. Moreover, GO incorporation into the PLGA microspheres improved the biological performance of the scaffolds. GO did not elicit any cytotoxic effects on adipose stem cells in vitro and all concentrations were shown to be well-tolerated by the cells. The PLGA/GO scaffolds were shown to significantly promote osteogenic differentiation in stem cells by increasing ALP activity or calcium mineral deposition. These results indicate that composite PLGA/GO microsphere scaffolds can be used as mechanically competent and biologically active scaffolds for load-bearing bone applications and for bone regenerative engineering.

MATERIALS AND METHODS

Scaffold Fabrication

Poly(DL-lactide-co-glycolide) (PLGA 85:15 lactide to glycolide ratio, $M_w$=152 kDa, IV=076–0.85 dL/g) was purchased from DURECT Corporation (Birmingham, AL). Graphene oxide sheets (7 96034 Aldrich) and polyvinyl alcohol (PVA, 87-90% hydrolyzed, average $M_w$ 30,000-70, 000) were purchased from Sigma-Aldrich. Methylene chloride was purchased from Fisher Scientific.

PLGA and PLGA/GO microspheres were prepared using an oil-in-water emulsion solvent evaporation method. For pure PLGA microspheres, PLGA was dissolved in methylene chloride at a ratio of 1:7.5 (w/v). To prepare composite PLGA/GO microspheres, GO was mixed with PLGA at various concentrations of 1, 3, 5 and 10 wt. %. The mixture was then dispersed in methylene chloride and vortexed until a homogeneous suspension was obtained. The suspensions were then added via a thin stream into a 1% (w/v) PVA solution under a stirring speed of 250 rpm and left overnight. The resultant microspheres were then collected, rinsed with deionized water, dried by vacuum filtration, and lyophilized. The microspheres were subsequently sieved to 300-600 μm size ranges and packed into stainless steel molds and heated at 90° C. for 90 min to create 3D porous structures of 5 mm diameter×5 mm height, 5 mm diameter×15 mm height, 3.5 mm diameter×1 mm height, or anatomically engineered shapes and dimensions.

Scaffold Characterization

Scanning Electron Microscopy (SEM)
SEM was used to investigate the structure and morphology of the microspheres and microsphere scaffolds. All samples were mounted, sputter coated with gold-palladium, and imaged using a FEI Nova NanoSEM™ 450 at a working distance of 5 mm and an acceleration voltage of 18 kV.
Thermogravimetric Analysis (TGA)
A TGA Q500 (TA Instruments) was used to investigate the presence and encapsulation of $CaO_2$ within the composite microspheres. TGA was performed under nitrogen gas over a temperature range from 50 to 500° C. with a ramp rate of 10° C. $min^{-1}$.
Mechanical Testing
Cylindrical scaffolds of 5 diameter×5 mm height were subjected to uniaxial compressive mechanical loading using an Instron™ 5544 mechanical tester. Mechanical testing was carried out at a crosshead speed of 2 mm/min until 60% displacement. The compressive stiffness, strength, and toughness of the samples were subsequently measured from the obtained stress-strain curves.

Cell Culture

Human adipose-derived stem cells (hADSCs, StemPro™) and all cell culture reagents were purchased from Invitrogen. DMSO was purchased from Sigma-Aldrich. Human ADSCs were cultured according to the supplier's specifications. Cells were expanded in MesenPRO RS™ basal medium supplemented with 2% MesenPRO RS™ growth supplement, 0.5% penicillin/streptomycin, and 1% L-glutamine). At P3, the cells were frozen down in freezing medium consisting of 50% growth medium, 40% MSC-qualified FBS, and 10% DMSO. All in vitro experiments were performed with cells at P5.
In Vitro Cytocompatibility
In order to sterilize the scaffolds, they were immersed in 70% ethanol for 20 min, washed with DPBS once, and subsequently exposed to UV radiation for 30 min on each side. The scaffolds were then placed in ultra-low attachment 96-well plates and seeded with cells at a density of 50,000 cells/scaffold in 5 μl of media. The cells were allowed to adhere to the scaffolds for 1 h before adding growth media to the wells. The culture was maintained for the duration of the experiments with regular media changes every 2 or 3 days. The viability of the cells was investigated using the CCK8 kit (Dojindo Molecular Technologies, Inc) and the LIVE/DEAD® assay (Invitrogen) at days 1, 3, 7, and 14, according to manufacturer specifications.
CCK8: The media was replaced with the CCK8 solution (20 μl CCK8, 230 μl growth media). After 2 h of incubation, the samples were added in triplicate to 96 well plates and absorbance values were measured at 450 nm using a TECAN™ plate reader.
Live/Dead assay: The scaffolds were rinsed once with DPBS and incubated with the Live/Dead solution (5 μl Calcein AM, 20 μl ethidium homodimer-1, 10 ml DPBS) for 15 min Imaging was carried out using confocal microscopy (Zeiss LSM Confocor2™ at 10× magnification). Quantification was performed by taking 4 random images from different field of views and measuring the pixel intensity.
Osteogenic Differentiation
Scaffolds were sterilized, incubated in DPBS for 3 days prior to use, and seeded with cells as described in the previous section. The culture was maintained in growth media for 3 days and then switched to osteogenic differentiation media, with regular media changes every 3 or 4 days. The osteogenic differentiation media consisted of StemPro® osteocyte/chondrocyte differentiation basal medium supplemented with 10% StemPro® osteogenesis supplement and 0.5% penicillin streptomycin.
Alkaline phosphatase (ALP) activity: The ALP activity was measured using the alkaline phosphatase (ALP) substrate kit (Bio-Rad, Hercules, CA). At day 28, the samples were transferred to new well plates, rinsed with DT water, and lysed using 1% Triton X-100 before being subjected to three freeze-thaw cycles. Next, 50 μL of the ALP substrate solution was added to 50 μL, of the cell lysate and incubated at 37° C. for 15 min. the reaction was stopped by adding 100 μL, of 0.4 M NaOH per well. Absorbance values were measured in triplicate at 405 nm using a TECAN plate reader. The ALP activity was subsequently normalized to total protein concentration using the Pierce™ BCA Protein Assay Kit (#23227, ThermoFisher).

Alizarin red S staining: Mineralized matrix synthesis was evaluated using the alizarin red S stain (Sigma-Aldrich) to identify calcium deposition. At day 28, the samples were transferred to new well plates, rinsed with DI water and fixed in 70% ethanol for 1 h at 4° C. The samples were then air-dried for 5 to 10 min, washed once with DI water, and incubated in the alizarin red S dye for 10 min at room temperature in the dark. The stained samples were subsequently washed with DI water several times. Quantification was performed by extracting the alizarin red S stain using a 10% cetylpyridinium chloride (CPC) solution. After 30 min of incubation at room temperature, the absorbance of the resulting solution was measured at 562 nm using a TECAN™ plate reader. Absorbance values from scaffolds with no cells were subtracted to eliminate the interference of the scaffolding material. Samples were analyzed in n=5.

Results

SEM imaging revealed a smooth exterior for all microspheres, irrespective of their chemical composition (See FIG. 1). TGA quantitatively corroborated the presence of increasing concentrations of GO, as the initial GO wt. % increased (see FIG. 2). WAXS results similarly confirmed the incorporation of GO sheets within the PLGA microspheres. (see FIG. 3).

Scaffolds were subjected to uniaxial compressive loading and stress-strain curves were generated. The stress-strain curves of sample P5GO behaved similar to trabecular bone under compressive loading (see FIG. 4). The addition of GO to the micropsheres significantly enhanced the compressive strength, Young's modulus (stiffness), and toughness of the composite scaffolds.

Human adipose stem cells were cultured on the scaffolds. In vitro studies demonstrated the biocompatibility and non-toxicity of the composite graphene matrices. (see FIG. 5). Human adipose stem cells were cultured on the scaffolds and assessed for bone differentiation. The cells cultured on sample P5GO demonstrated a significant increase in osteogenic differentiation, as was measured by ALP activity and Alizarin red S assay (see FIG. 6).

Conclusions: These results indicate that the incorporation of GO sheets into PLGA microspheres presents an effective approach to develop scaffolds that are both mechanically competent and biologically active for bone tissue regeneration.

We claim:

1. A porous scaffold, comprising a plurality of microspheres, wherein each microsphere in the plurality of microspheres comprises a polymer blended with a graphene family material (GFM), wherein the polymer comprises poly(L-lactic-co-glycolic acid) (PLGA), and wherein the GFM is selected from the group consisting of graphene oxide, reduced graphene oxide, functionalized derivatives thereof, and combinations thereof.

2. The porous scaffold of claim 1, wherein the plurality of microspheres are joined to form the porous scaffold by sintering the plurality of microspheres together.

3. The porous scaffold of claim 1, wherein the polymer blended with a GFM comprises GFM encapsulation into the polymer.

4. The porous scaffold of claim 1, wherein the GFM is present at between about 1% to about 10% as a wt % of the porous scaffold, or between about 1% to about 5% as a wt % of the plurality of microspheres.

5. The porous scaffold of claim 1, wherein the plurality of microspheres are between about 100 μm in diameter and about 1000 μm in diameter.

6. The porous scaffold of claim 1, wherein a ratio of carbon atoms to oxygen atoms of the GFM is between about 2:1 to about 4:1.

7. The porous scaffold of claim 1, wherein at least 50% of the plurality of microspheres are joined to one or more other microspheres in the porous scaffold.

8. The porous scaffold of claim 1, wherein the porous scaffold is between about 1 mm×1 mm and about 20 mm×20 mm (diameter×height).

9. The porous scaffold of claim 1, further comprising cells, growth factors, small molecules, therapeutics, and/or diagnostic agents on or in the porous scaffold.

10. A microsphere, comprising a polymer blended with a GFM, wherein the polymer comprises poly(L-lactic-co-glycolic acid) (PLGA), and wherein the GFM is selected from the group consisting of graphene oxide, reduced graphene oxide, functionalized derivatives thereof, and combinations thereof.

11. The microsphere of claim 10, wherein the GFM comprises graphene oxide or reduced graphene oxide.

12. The microsphere of claim 10, wherein the GFM is encapsulated in the polymer.

13. The microsphere of claim 10, wherein the GFM is present at between about 1% to about 10% as a wt % of the microsphere, or between about 1% to about 5% as a wt % of the microsphere.

14. The microsphere of claim 10, wherein the microsphere is between about 100 μm in diameter and about 1000 μm in diameter.

15. The microsphere of claim 10, wherein a ratio of carbon atoms to oxygen atoms of the GFM is between about 2:1 to about 4:1.

16. The microsphere of claim 10, further comprising cells, growth factors, small molecules, therapeutics, and/or diagnostic agents associated with the microsphere.

17. A method for replacement and/or regeneration of bone tissue, comprising administering to a subject in need thereof the porous scaffold of claim 1 to promote replacement and/or regeneration of bone tissue in the subject.

18. A method for making the porous scaffold or microsphere of claim 1, comprising
   (a) dissolving a polymer comprising poly(L-lactic-co-glycolic acid) (PLGA) in a solvent to produce a dissolved polymer;
   (b) mixing the dissolved polymer with a GFM, wherein the GFM comprises graphene oxide (GO) or reduced graphene oxide (rGO), to form a mixture;
   (c) dispersing the mixture in the solvent to generate a homogeneous suspension; and
   (d) adding the homogenous suspension into a solvent solution and stirring to form the porous scaffold.

* * * * *

UNITED STATES PATENT AND TRADEMARK OFFICE
CERTIFICATE OF CORRECTION

| | | |
|---|---|---|
| PATENT NO. | : 12,091,522 B2 | Page 1 of 1 |
| APPLICATION NO. | : 17/598428 | |
| DATED | : September 17, 2024 | |
| INVENTOR(S) | : Cato Laurencin et al. | |

It is certified that error appears in the above-identified patent and that said Letters Patent is hereby corrected as shown below:

In the Specification

Column 1, Lines 4-8 should recite as follows:
CROSS REFERENCE
This application is a U.S. national phase of International Application No. PCT/US2020/025906, filed on March 31, 2020, which claims priority to U.S. Provisional Patent Application Serial No. 62/828149, filed April 2, 2019, both of which are incorporated by reference herein in their entirety.

Column 1, Lines 10-17 should recite as follows:
STATEMENT OF GOVERNMENT RIGHTS
This invention was made with government support under grant number DP1-AR-068147 awarded by the National Institutes of Health. The government has certain rights in the invention.

Signed and Sealed this
Twenty-ninth Day of October, 2024

Katherine Kelly Vidal
*Director of the United States Patent and Trademark Office*